(12) United States Patent
Schupp et al.

(10) Patent No.: US 7,768,637 B2
(45) Date of Patent: Aug. 3, 2010

(54) METHOD FOR ACQUIRING HIGH-RESOLUTION IMAGES OF DEFECTS ON THE UPPER SURFACE OF THE WAFER EDGE

(75) Inventors: Detlef Schupp, Neunkirchen (DE); Thin Van Luu, Wetzlar (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 373 days.

(21) Appl. No.: 12/072,156

(22) Filed: Feb. 25, 2008

(65) Prior Publication Data

US 2008/0204738 A1    Aug. 28, 2008

(30) Foreign Application Priority Data

Feb. 28, 2007    (DE) .................. 10 2007 010 225

(51) Int. Cl.
*G01N 21/00* (2006.01)
(52) U.S. Cl. .................................. 356/237.5
(58) Field of Classification Search ........... None
See application file for complete search history.

(56) References Cited

U.S. PATENT DOCUMENTS

| | | | |
|---|---|---|---|
| 6,476,388 B1 * | 11/2002 | Nakagaki et al. | 850/9 |
| 2006/0119366 A1 | 6/2006 | Iffland et al. | 324/500 |
| 2006/0119367 A1 | 6/2006 | Iffland et al. | 324/500 |
| 2007/0057184 A1 * | 3/2007 | Uto et al. | 250/310 |

FOREIGN PATENT DOCUMENTS

| DE | 10 2004 058 126 | 6/2006 |
|---|---|---|
| DE | 10 2004 058 128 | 6/2006 |

* cited by examiner

*Primary Examiner*—Tu T Nguyen
(74) *Attorney, Agent, or Firm*—Davidson, Davidson & Kappel, LLC

(57) ABSTRACT

A method for acquiring high-resolution images of defects on the upper surface of the wafer edge is disclosed. For this purpose, first the position of at least one defect on the upper surface of the wafer edge is determined. The thus determined position of the defect is stored. Then the wafer is transferred into device for micro-inspection, in which the defect is examined more closely and imaged. The images acquired in the device for micro-inspection are deposited in a directory.

18 Claims, 7 Drawing Sheets

METHOD FOR ACQUIRING HIGH-RESOLUTION IMAGES OF DEFECTS ON THE UPPER SURFACE OF THE WAFER EDGE

This claims priority to German Patent Application No. 10 2007 010 225.0, filed on Feb. 28, 2007, the entire disclosure of which is incorporated by reference herein.

The present invention relates to a method for acquiring high-resolution images of defects on the upper surface of the wafer edge.

BACKGROUND

The German published application DE 102004058128 A1 discloses a system for inspecting a disc-shaped object. The device suggested therein allows to capture the front and back of the disc-shaped object at the same time. Although the device suggested therein allows to capture the front of a wafer so that the representation of the wafer edge is also possible, this macro-representation does not allow the acquisition of high-resolution images of defects on the upper surface of the wafer edge.

The German published application DE 102004058126 A1 also reveals a device for inspecting the front and back of a disc-shaped object. Also the whole area of the wafer and thus also the wafer edge is captured. The device does not allow detailed representation or imaging of defects on the upper surface of the wafer edge either.

The automatic acquisition of defect images on the wafer edge involves the problem that defects too near the edge cannot be focused on.

SUMMARY OF THE INVENTION

It is an object of the present invention to provide a method for acquiring high-resolution images of defects on the upper surface of the wafer edge without focusing problems reducing the quality of the acquired image.

The present invention provides a method for acquiring high-resolution images of defects on the upper surface of the wafer edge. One step is, providing the position of at least one defect on the upper surface of the wafer edge. Next, a transfer of the wafer into a device for micro-inspection is carried out. A focusing on each defect is carried out in the device for micro-inspection, wherein an appropriate focusing method is selected depending on the position of the defect with respect to the wafer edge. Next at least one defect is imaged in the device for micro-inspection using a microscope including several objectives of various magnifications, wherein the objective with which the defect may be detected best is selected for imaging. Finally, the images of the at least one defect are stored in a directory.

The method is particularly advantageous if first the position of at least one defect on the upper surface of the wafer edge is determined. The position of at least one defect may, for example, be determined from the macro-image of the whole upper surface of the wafer. It is also possible to generate a macroscopic image of the whole wafer edge. Then the positions of the at least one defect found by macroscopic imaging of the wafer edge or the whole wafer surface are stored. Then the wafer is transferred into a device for micro-inspection. The device for micro-inspection also receives the data of the position of the at least one defect so that the positions of the defects may be approached correspondingly. In the device for micro-inspection, it is possible to focus on each defect with various focusing methods. The defect is imaged in the device for micro-inspection by means of a microscope to which a camera is connected, the microscope having several objectives of various magnifications. For imaging, the objective with which the defect may be detected best is moved into the optical path. Finally, the acquired images of the at least one defect are deposited in a directory. For determining the position of the at least one defect on the upper surface of the wafer edge, the wafer is transported into the device for edge inspection. In the device for edge inspection, the position of the at least one defect is determined.

In the device for micro-inspection, the wafer can be automatically aligned. The automatic alignment may be performed both for a bare wafer and for a structured wafer.

The imaging of the defects can be conducted automatically, wherein a laser focus, a TV focus or combinations of both focusing methods are used to focus on a defect. The use of the appropriate focusing method depends on the position of the defect with respect to the edge of the wafer.

The criterion determining at what point a certain focusing criterion is used depends on the position of the defect with respect to the edge of the wafer. The user may set a radius for the wafer from where the appropriate focus criterion may be used.

Laser focus can be exclusively used for defects that, for a predetermined value of the radius, are located nearer to the center of the wafer.

For defects that, for a predetermined value of the radius, are located nearer to the edge of the wafer, first an X/Y position can be taken up that is positioned in the proximity of the actual defect but nearer to the center of the wafer. Then the laser focus can be used for focusing at this position, and then the laser focus is turned off. After returning to the defect with the focus setting thus determined, images of the defect are acquired.

For defects that, for a predetermined value of the radius, are located nearer to the edge of the wafer, first the laser focus can be used to focus at the position of the defect, thus determining a focal position for the laser focus. The laser focus can be turned off and a TV focus is moved to some distance from the focal position of the laser focus. Several images are acquired in an interval around the focal position of the laser focus.

A scan performing automatic defect centering can be added upstream in the device for micro-inspection if the defect is outside the field of view of the currently used objective of the microscope because of the imprecise position determination in the device for macro-inspection, wherein the defect position is not determined with the help of reference images, but with the defect image itself.

For choosing the appropriate focusing method, there can be first a test whether the defect to be focused on is outside a predetermined radius with respect to the wafer edge. The TV focus or the laser focus is used if the defect is within a predetermined radius.

After the laser focus is turned off, the Z position of a Z drive for the optimal laser focus can be stored. The Z drive is used to reach the start position for the image acquisition with the TV focus. The start position for the TV focus is always ΔZ away from the focal position of the laser focus. The TV focus is moved in an interval around the focal position of the laser focus. When a definition criterion is reached or after a Z interval has been completed, the Z position stored at the beginning is taken up again, and the best image with respect to definition is stored. After the scan has been completed, the wafer is returned into a cartridge connected to the system for optical inspection of wafers. The acquired images of the defects are stored in a directory to be chosen by the user. The images are deposited as reference in a KLARF (KLA Review File).

BRIEF DESCRIPTION OF THE DRAWINGS

In the following, the invention will be described exemplarily with reference to the accompanying drawings. Further features, objects and advantages of the present invention will become apparent from the accompanying drawings, in which.

DETAILED DESCRIPTION OF THE INVENTION

Figure 1:
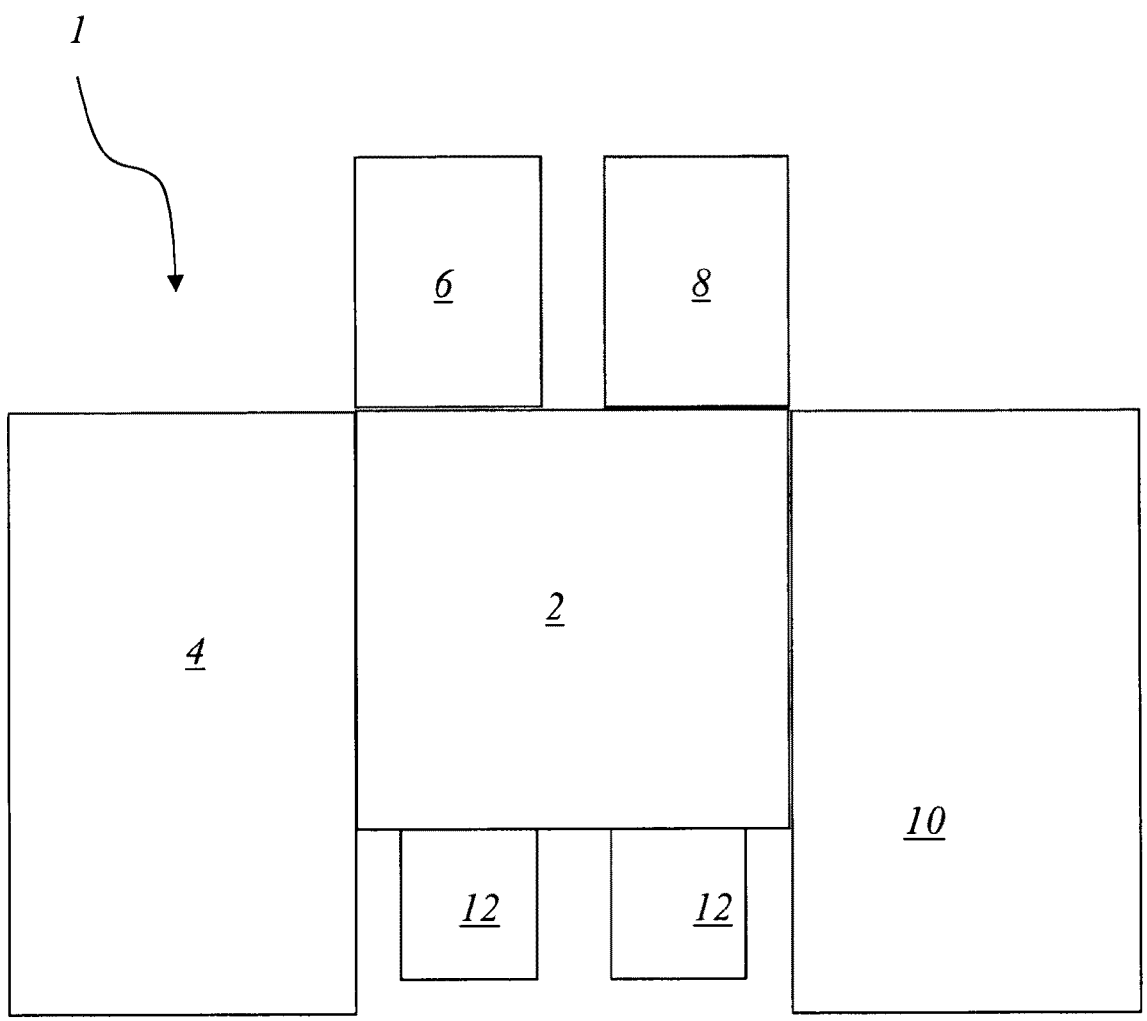
FIG. 1 shows a schematic illustration of a system for optical inspection of wafers.

In the figures, identical reference numerals refer to elements or functional groups that are identical or have basically the same effect.

FIG. 1 shows a system 1 for optical inspection of wafers. System 1 is designed as a modular construction. Several modules 4, 6, 8 and 10 performing various optical and/or non-optical examinations of the wafer are arranged around a central unit 2. The central unit may itself perform examinations of the wafer. Essentially, the central unit 2 is responsible for transporting each wafer to the various modules 4, 6, 8 and 10. The central unit 2 is also connected to two load ports 12. The wafers to be examined may be supplied to the system 1 via the load ports 12. The modules 4, 6, 8 and 10 connected to the central unit 2 may be provided for various optical and/or non-optical examinations of the wafer, module 4 may, for example, be provided for macro-inspection of the wafer. Module 10 may be used for micro-inspection. There, for example, positions on the wafer found in module 4 for macro-inspection may be examined and inspected more closely. Central unit 2 is also responsible for transporting the wafers between any of the modules 4, 6, 8 and 10. For example, an edge inspection and/or an inspection of the back of a wafer may be performed with the modules 6 and/or 8 connected to the central unit. Thus the integration of the method for acquiring high-resolution images of defects on the upper surface of the wafer is integrated in the module for micro-inspection.

Figure 2:
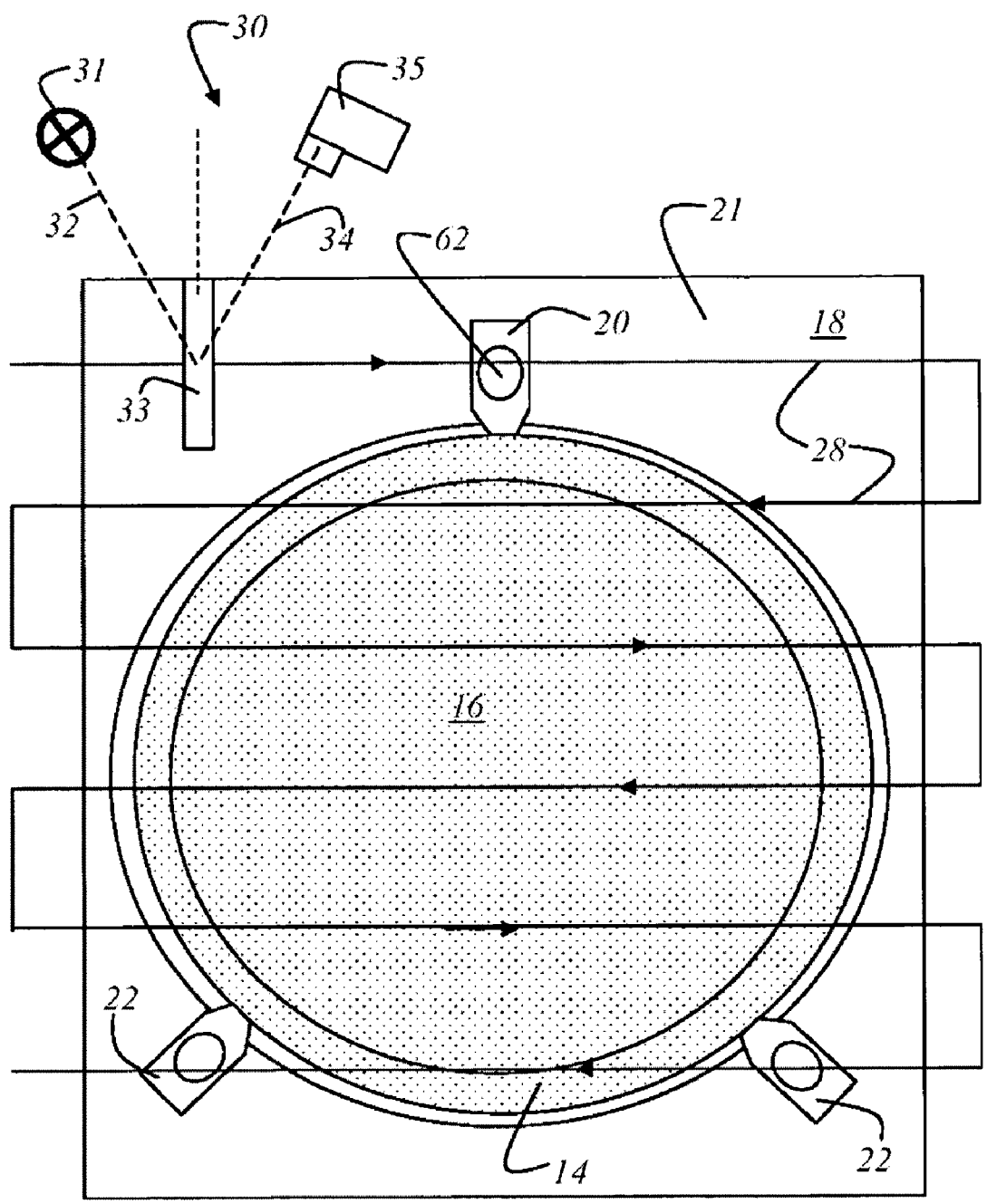
FIG. 2 shows a schematic illustration of an embodiment for acquiring an overview image of a whole surface of a wafer.

FIG. 2 shows a schematic illustration of a device for acquiring macroscopic images of the surface of a wafer 16. The wafer 16 is located in a wafer holder 18. Mechanical contact elements 20 may be provided for fixing the wafer 16 in the wafer holder. An optical scanner 30 is arranged above the wafer holder 18, with which images of the surface of the wafer holder 18 and thus all objects present on the wafer holder 18 (wafer 16) may be acquired. The optical device 30 is moved along a meandering path 28 above the surface 21 of the wafer holder 18.

Other arrangements may be provided for capturing the surface 21 of the wafer holder 18 or only the wafer 16. The arrangement for optically capturing the surface 21 of the wafer holder 18 includes a light source 31 emitting a light beam 32. An illuminated field 32 is formed on the surface 21 of the wafer holder 18, which moves along the meandering path 28 across the surface 21 of the wafer holder 18 corresponding to the relative movement between the wafer holder 18 and the capturing device 30. The light 34 from the surface 21 of the wafer holder 18 reaches a camera 35 acquiring an image of the respective illuminated spot 33. The images of each illuminated spot 33 are combined to form an overall image of the wafer holder 18 and thus the wafer 16. The edge 14 of the wafer may also be seen in the overall image of the wafer 16. The capturing device 30 allows to capture the surface of both a structured wafer and an unstructured wafer (bare wafer).

It is also conceivable that the whole surface of the wafer is captured in one scan. This is, for example, comparable to scanning a conventional original for copying.

Figure 3:
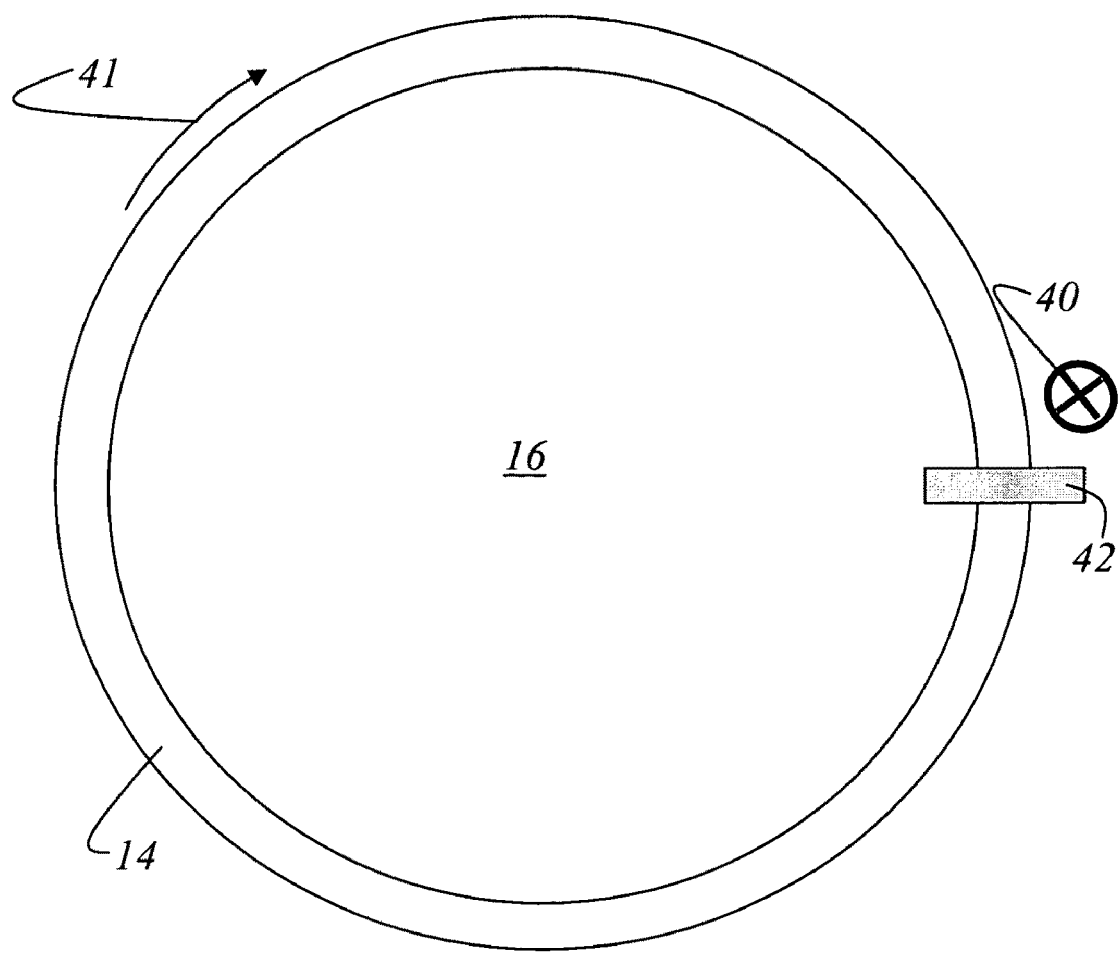
FIG. 3 shows a schematic illustration for acquiring an overview image (macroscopic image) of the whole upper surface of a wafer edge.

FIG. 3 is a schematic illustration of an arrangement in which only the edge area 14 of the wafer 16 is captured. The wafer is rotated in the direction of arrow 41 illustrated in FIG. 3. The wafer 16 is rotated by rotating means not shown. A camera 42, which serves for acquiring an image of the edge area 14 of the wafer 16, is provided opposite the edge area 14. The edge area 14 of the wafer 16 is captured as the wafer 16 passes beneath the camera 42. A light source 40 is associated with the camera 42 and/or the wafer 16 such that the edge area 14 of the wafer 16 is illuminated. After the wafer 16 has completed a revolution of slightly more than 360°, an image of the edge area 14 of the wafer 16 is obtained. Defects can be detected in the imaged edge area, and a precise location can be associated with these defects as a function of the rotation angle and the position of the defect in the camera image. The edge area 14 may be set by a user such that it defines a radius. Conventional focusing methods are used for all defects within this radius. If the defect is outside the radius, i.e. nearer to the edge of the wafer 16, the modified focusing method is used.

Figure 4:
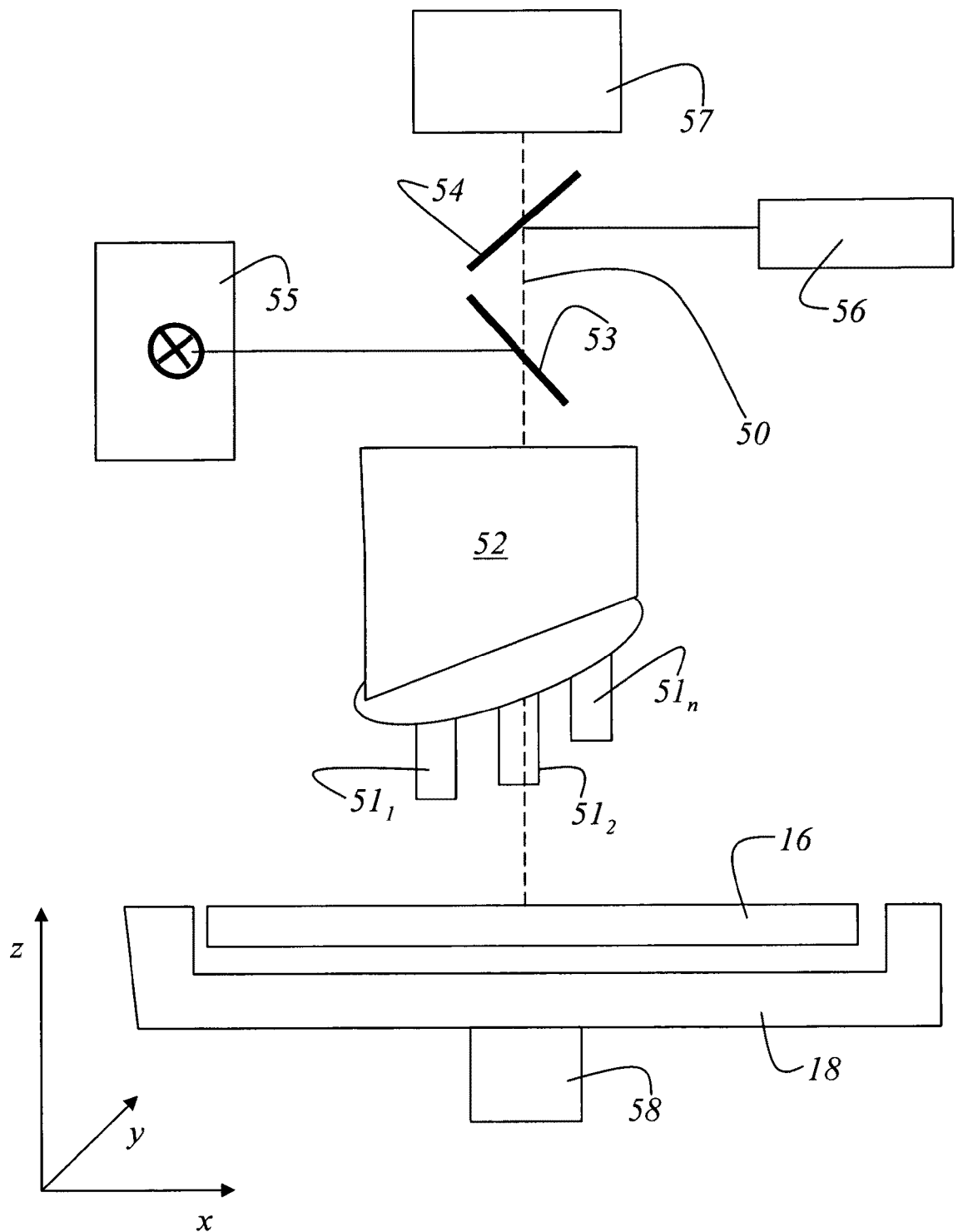
FIG. 4 shows a schematic illustration of the device for microscopic inspection of selected defects.

FIG. 4 shows a schematic arrangement of device 59 for micro-inspection of defects on the surface of a wafer 16. In the device 59 for micro-inspection, the wafer 16 is also inserted in a wafer holder 18. A relative movement in the X and Y direction may be performed between the device 59 for micro-inspection and the wafer holder, so that each defect found during macro-inspection may be approached and subjected to closer inspection. Device 59 for micro-inspection further includes first focusing means 55 and second focusing means 56. The first focusing means 55 is a TV focus, wherein the light required for focusing is launched into the optical path 50 of the device 59 for micro-inspection using a beam splitter 53. The second focusing means 56 includes a laser focus, wherein the required light is also launched into the optical path 50 of device 59 for micro-inspection by means of a beam splitter 54. A drive 58 is provided for acquiring a series of images with the TV focus, the drive causing a relative movement between the microscope and the surface of the wafer 16 in the Z direction, so that several images or images of defects on the surface of the wafer 16 are captured one after the other in various focal positions.

Figure 5:
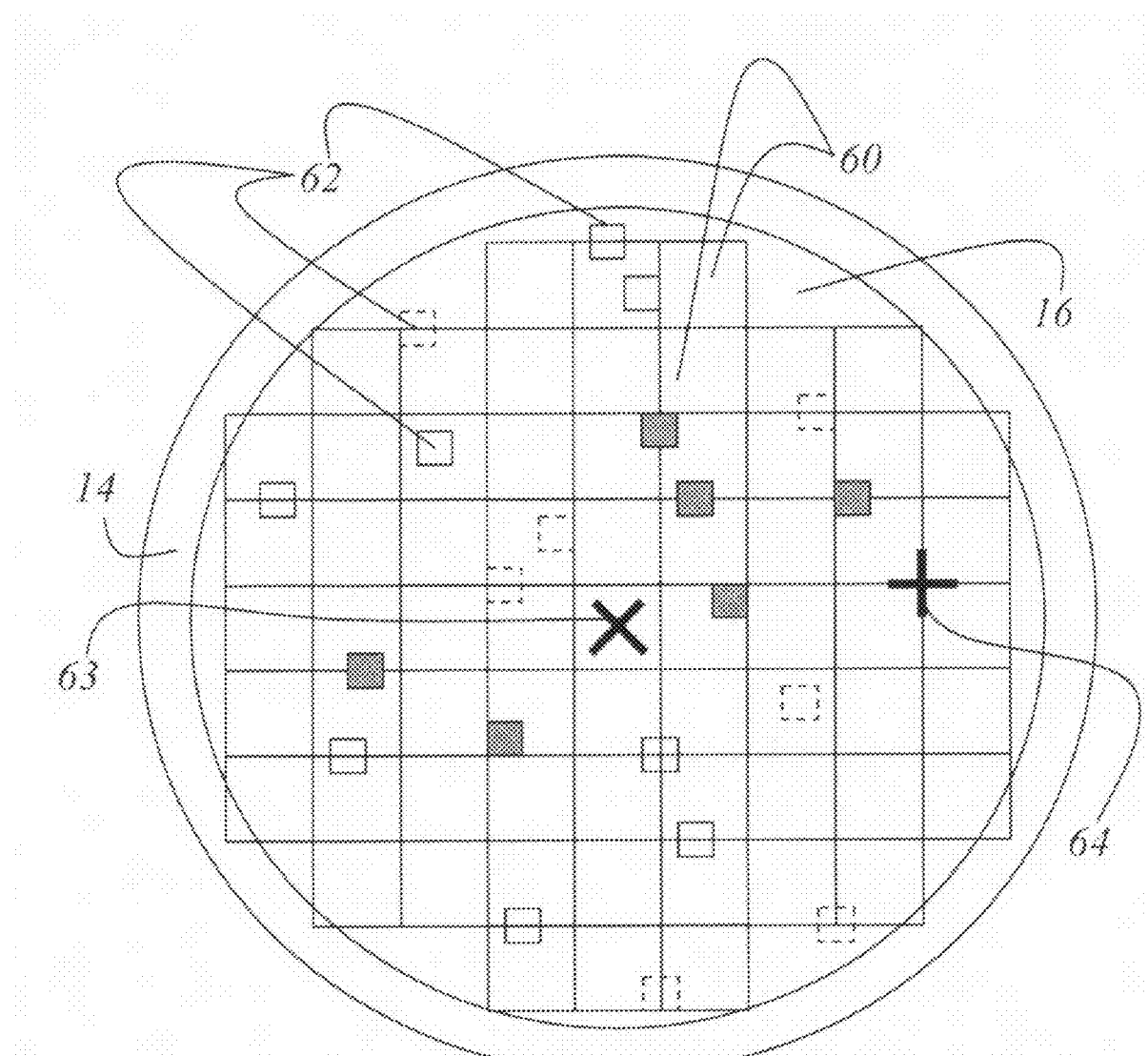
FIG. 5 shows a schematic illustration of the macroscopic image of the upper surface of a wafer.

From the load ports 12 of the system 1 for optical inspection of wafers, the wafers 16 are transported from a cartridge to means for capturing the surface of the wafer or the edge area of the wafer. The position of each defect in the area of the edge of the wafer 16 may also be determined in a wafer edge station. The determination of the position or site of each defect on the wafer edge is done automatically. FIG. 5 shows the macroscopic image of the surface of a wafer 16. In this case, a structured wafer is shown, wherein the dies 60 can already be seen on the surface. In the macroscopic image of the wafer 16, each defect is indicated and marked with various symbols. The macroscopic image of the surface of the wafer 16 does not always reveal whether the found defects are really defects. For closer examination, it is necessary to subject the wafer to a microscopic inspection in device for micro-inspection. For this purpose, the wafer is transported from the device for macro-inspection into the device for micro-inspection. As shown in FIG. 4, the device 59 for micro-inspection includes a microscope provided with several objectives $51_1$, $51_2$, ... $51_N$, which may be moved into the optical path as demanded. Based on the macroscopic image of the surface of the wafer 16 or the edge of the wafer 16, the position of each defect may be determined. These positions are then correspondingly approached in the device 59 for micro-inspection in order to subject the defects expected in these positions to closer examination. The wafer 16 is automatically aligned or subjected to automatic alignment in the device for micro-inspection. Now, images of the defects with various resolutions may be automatically acquired in the device for micro-inspection. The device 59 for micro-inspection is provided with first focusing means 55 and second focusing means 56. The first focusing means includes a TV focus, and the second focusing means 56 includes a laser focus. There may be positions in the area of the edge 14 of the wafer 16 where the laser focus fails. A special TV focus must be used for these positions. If an objective $51_1$ with 20-fold magnification is used in the device 59 for micro-inspection, the imaging must be preceded by a scan performing automatic defect centering. The defect position is not determined with the help of reference images, but with the defect image itself. After the scan has been completed, the wafer 16 is returned into the cartridge on the load port 12. The images are stored in a directory to be chosen by the user and deposited as reference in a KLARF (KLA Review File). When images of the defects on the wafer edge are acquired automatically, there is the problem that defects too near the edge cannot be focused on. In this case, the laser focus is turned off and the Z position is noted. For the start position for acquiring images, a Z offset is taken up. The movement in the Z direction is effected with constant speed by drive 58. During the movement, images are acquired and evaluated. A predetermined definition criterion is of interest, and when this definition criterion is reached or the area has been covered completely, there is a return to the Z position stored at the beginning (when the laser focus was turned off).

In order to achieve an automatic process not requiring any intervention by the user for the method for acquiring high-resolution images of defects on the upper surface of the wafer edge, there must be checked whether the defect to be examined is outside a predetermined radius. A corresponding focusing method must be used depending on the position of the defect. If the defect is within the radius, the laser focus for (normal) defects may be used. However, if the defect is outside the radius, first an X/Y position near the actual defect is taken up. This position is thus closer to the center of the wafer 18 and may thus be focused on by the laser focus. The laser focus is turned on and there is a waiting period until the focus is reached. Then the laser focus is turned off, and the X/Y coordinates of the defect are approached. The TV focus for edge defects is used and the best image is stored.

Figure 6:
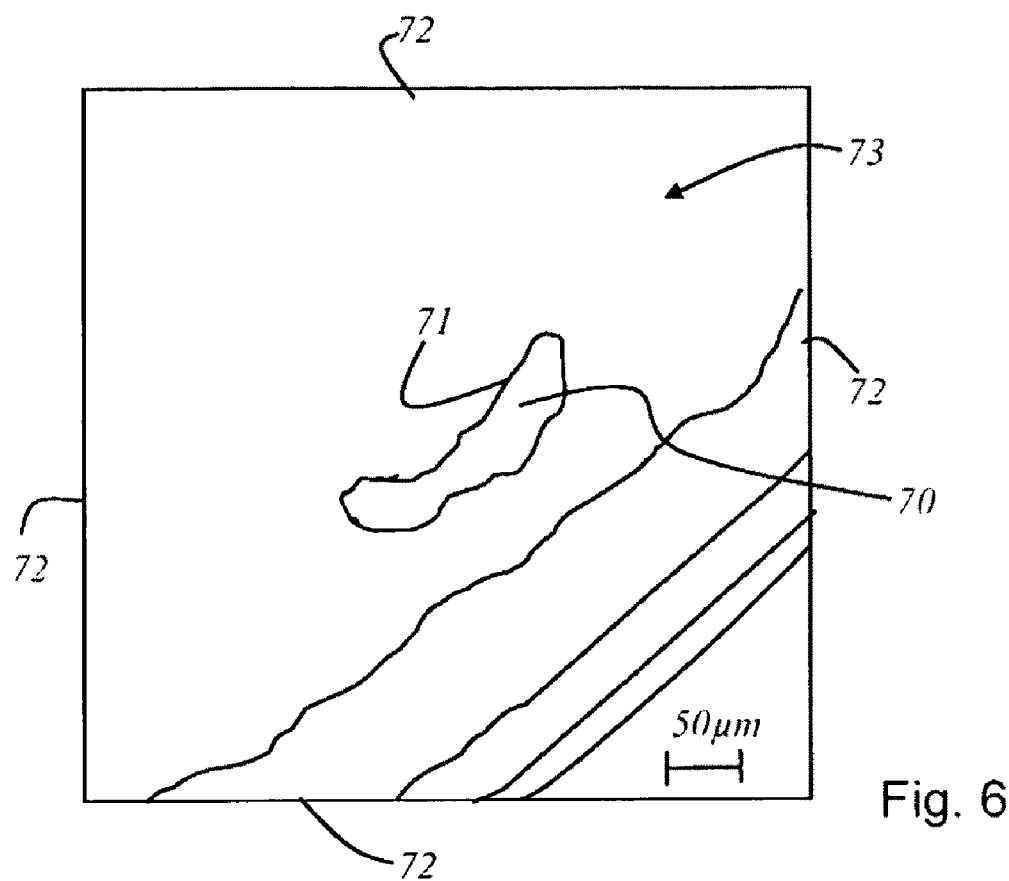
FIG. 6 shows an image of a defect near the edge of the wafer, which is detected as a defect if it is surrounded by a continuous line.

FIG. 6 shows a defect 70 near the edge 14 of the wafer 16. The defect 70 is only detected if it is completely enclosed. The meaning of "completely enclosed" is that the defect 70 is located completely in the image area 73 captured by the camera. In addition, the defect 70 may not cross two image boundaries 72 of the image area 73.

Figure 7:
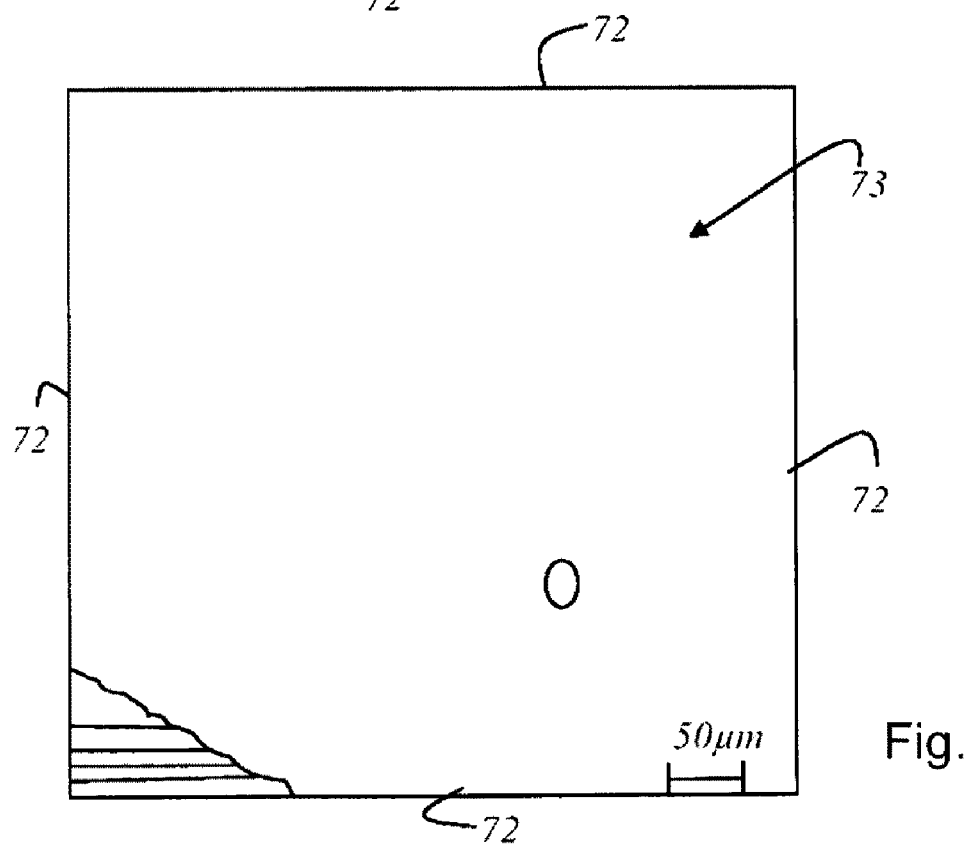
FIG. 7 shows an image of a defect on the upper surface of the wafer, wherein parts of the DIE structure can also be seen in the picture.

FIG. 7 shows the image of a defect 80 acquired with an objective of low magnification. There is the problem that the die structure may be in the image area 73 in addition to the defect 80. This may result in the die structure also being detected as a defect. Depending on the position of the defect on the wafer, the die structure may appear in all parts of the image area 73. Depending on the position of the defect 80, part of the image area 73 (where the structure is expected) is left out for the defect detection. Alternatively, it is also possible to choose another objective for defect centering with which the structure of the wafer is sure to disappear from the image area 73.

Figure 8:
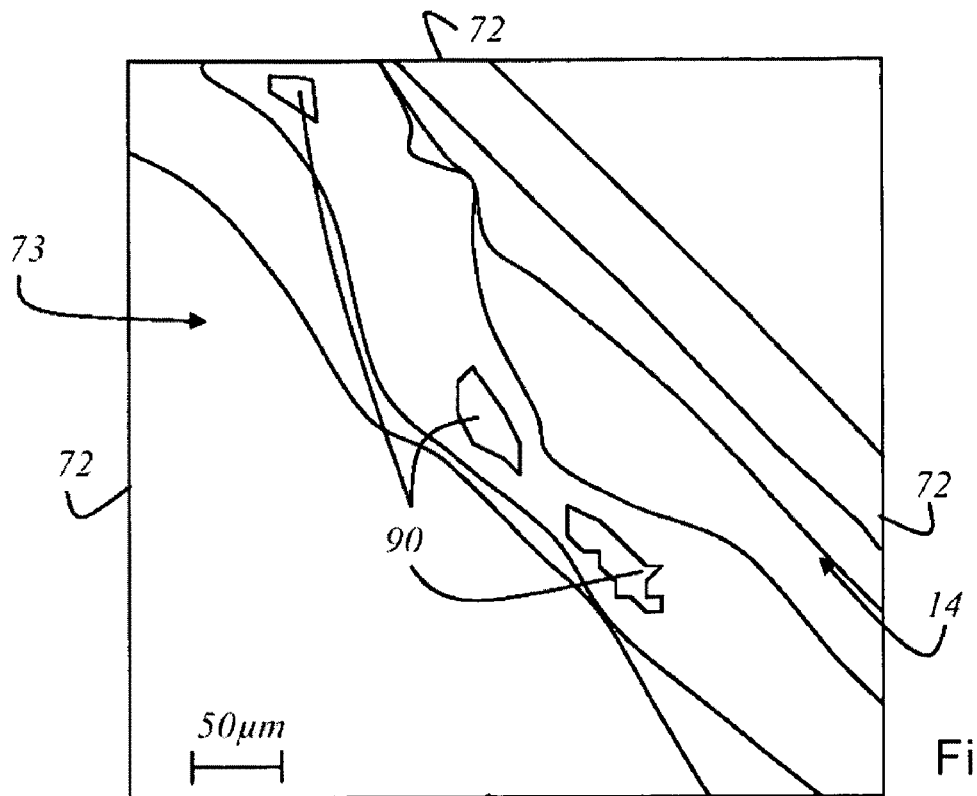
FIG. 8 shows an image of the wafer edge with several defects to be seen in the field of view.

FIG. 8 shows the problem that small defects 90 are not detected correctly, because the whole image area 73 is not homogeneous. This is mainly due to the wafer edge itself with its curved slope. One possibility is that only defects larger than a predetermined minimum size are detected as such defects. A further problem is shown in FIG. 8, which results from the use of objectives with, for example, 10-fold magnification. It may often be the case that several defects 90 are in the field of view 73. Thus there is the problem which of these defects is to be subjected to centering. One possibility is to select some defect criteria (for example length-to-width ratio) to identify a defect which is to be subjected to centering.

Figure 9:
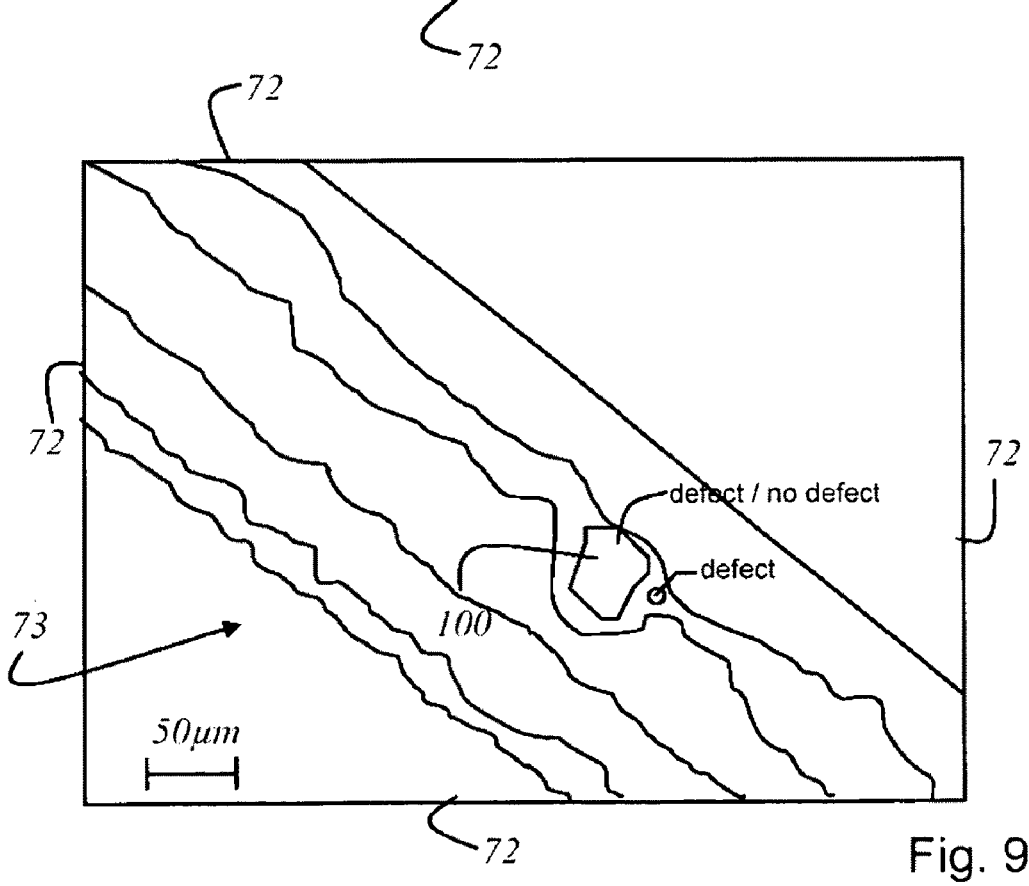
FIG. 9 shows an illustration of the image of the wafer edge with a low-contrast defect located near the wafer edge.

FIG. 9 shows a further problem resulting from low-contrast defects 100 near the wafer edge. One possible solution is to introduce a threshold value which is used for detecting defects. If the contrast value for a potential defect exceeds this threshold value, this potential defect is identified as a real defect. If the contrast value for the potential defect is below the threshold value, this potential defect is not identified or classified as a defect.

What is claimed is:

1. A method for acquiring high-resolution images of defects on an upper surface of a wafer edge, comprising the steps of:
   providing a position of at least one defect on the upper surface of the wafer edge;
   transferring the wafer into a device for micro-inspection;
   focusing on each defect in the device for micro-inspection, wherein an appropriate focusing method is selected depending on the position of the defect with respect to the wafer edge;
   imaging the at least one defect in the device for micro-inspection using a microscope including several objectives of various magnifications, wherein a first objective most suitable for detecting the defect is selected for imaging; and
   depositing images of the at least one defect in a directory.

2. The method of claim 1, wherein the position of the defect with respect to the wafer edge is determined by a radius set by a user.

3. The method of claim 1, wherein providing the position of at least one defect is performed via a review file.

4. The method of claim 1, wherein providing the position of at least one defect is performed by a device for macro-inspection.

5. The method of claim 4, wherein the whole surface of the wafer is captured with the device for macro-inspection.

6. The method of claim 4, wherein the wafer is transported into the device for edge inspection for determining the position of the at least one defect on the upper surface of the wafer edge, and that the position of the at least one defect is determined in the device for edge inspection.

7. The method of claim 1, wherein a laser focus is used for defects that, for a predetermined value of the radius, are located nearer to the center of the wafer.

8. The method of claim 1, wherein a TV focus is used for defects that, for a predetermined value of the radius, are located further from the center of the wafer.

9. The method of claim 1, wherein, for defects that, for a predetermined value of the radius, are located nearer to the edge of the wafer, first an X/Y position is taken up that is located in the proximity of the actual defect but nearer to the center of the wafer, that the laser focus is used for focusing at this position, that the laser focus is turned off, and that there is a return to the defect with this focus setting.

10. The method of claim 1, wherein, for defects that, for a predetermined value of the radius, are located nearer to the edge of the wafer, first an X/Y position is taken up that is located in the proximity of the actual defect but nearer to the center of the wafer, that the laser focus is used for focusing at this position, that the laser focus is turned off, that a TV focus is moved to some distance from the focal position of the laser focus, and that several images are acquired in an interval around the focal position of the laser focus.

11. The method of claim 1, wherein an automatic alignment of the wafer is performed in the device for micro-inspection.

12. The method of claim 11, wherein the automatic alignment is performed with a bare wafer.

13. The method of claim 11, wherein the automatic alignment is performed with a structured wafer.

14. The method of claim 1, wherein a scan performing automatic defect centering is added upstream in the device for micro-inspection if the defect is located outside a field of view of a currently used objective because of the imprecise position determination in the device for macro-inspection, and wherein the defect position is not determined with the help of reference images, but with the defect image itself.

15. The method of claim 14, wherein a Z drive is moved with constant speed, and that images are acquired and evaluated during the movement.

16. The method of claim 15, wherein, when a definition criterion is reached or after a Z interval has been completed, the Z position stored at the beginning is taken up again, and that the best image with respect to definition is stored.

17. The method of claim 1, wherein the wafer is returned into the cartridge connected to a system for optical inspection of wafers after the scan has been completed, and the acquired images of the defects are stored in a directory to be chosen by the user.

18. The method of claim 17, wherein the images are deposited as reference in a KLA Review File.

* * * * *